United States Patent [19]

Hussain et al.

[11] Patent Number: 4,885,287

[45] Date of Patent: Dec. 5, 1989

[54] NOVEL METHOD OF ADMINISTERING ASPIRIN AND DOSAGE FORMS CONTAINING SAME

[75] Inventors: Anwar A. Hussain; Lewis W. Dittert, both of Lexington; Thomas S. Foster, Nicholasville, all of Ky.

[73] Assignee: University of Kentucky Research Foundation, Lexington, Ky.

[21] Appl. No.: 229,963

[22] Filed: Aug. 9, 1988

[51] Int. Cl.4 ............................................. A61K 31/60
[52] U.S. Cl. .................................................... 514/159
[58] Field of Search .......................................... 574/159

[56] References Cited

U.S. PATENT DOCUMENTS 4,778,810 10/1988 Wenig et al. ...................... 514/263

Primary Examiner—Stanley J. Friedman
Attorney, Agent, or Firm—Burns, Doane, Swecker & Mathis

[57] ABSTRACT

The invention relates to a novel method of administering aspirin to achieve improved delivery thereof. The invention further relates to novel dosage forms of neutralized aspirin adapted for nasal administration, such as solutions, suspensions, gels and ointments. These dosage forms find utility in the treatment of conditions known to respond to the administration of aspirin, particularly in the treatment of migraine and in the mitigation of cardiovascular damage resulting from heart attack.

24 Claims, 1 Drawing Sheet

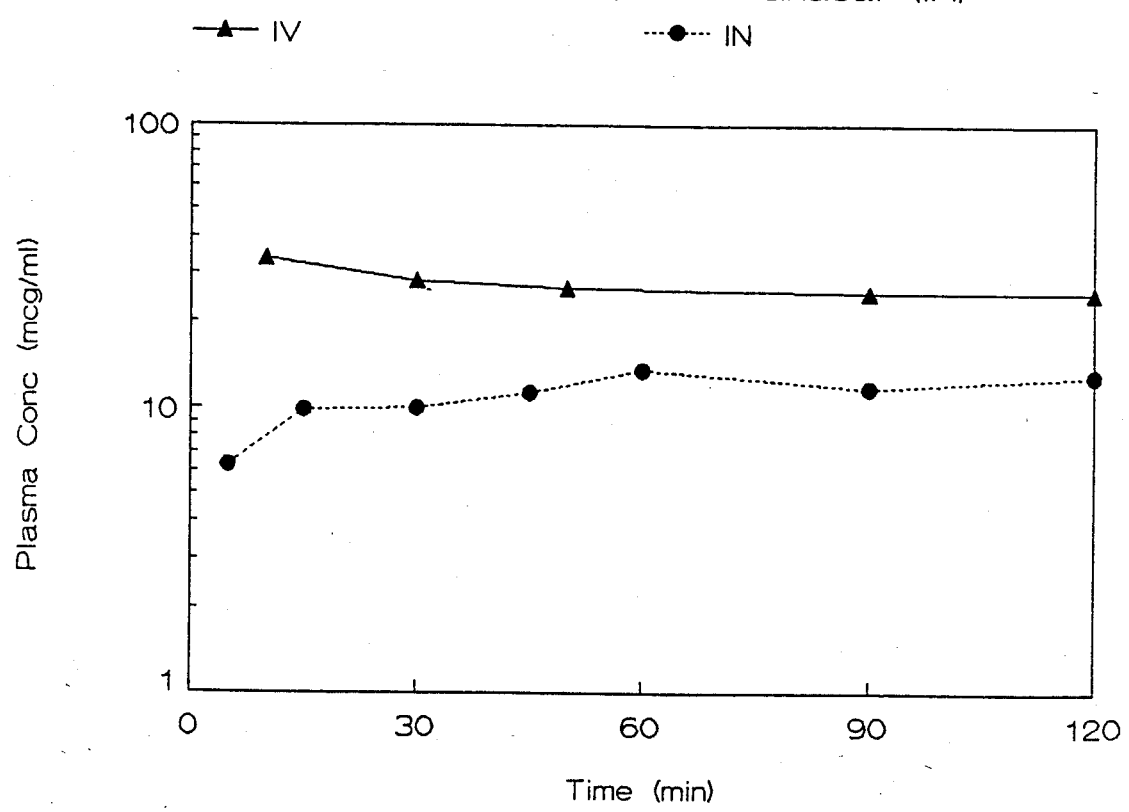

NOVEL METHOD OF ADMINISTERING ASPIRIN AND DOSAGE FORMS CONTAINING SAME

BACKGROUND OF THE INVENTION

1. Field of the Invention

The present invention relates to a novel method of administering aspirin, and to novel dosage forms containing same which are adapted for nasal administration.

2. Background Art

Aspirin is a well-known analgesic, antipyretic and anti-inflammatory agent widely used in the treatment of pain, fever and inflammation. It is particularly useful in the treatment of acute pain, such as post-operative pain.

Aspirin has been used in the recent past in the treatment of migraine, but with varying degrees of success. See, for example, Ross-Lee et al, *Cephalalgia*, Vol. 2, 9–14 (1982) and other studies referred to therein. Ross-Lee et al found that oral aspirin (900 mg) frequently relieved the pain of migraine attacks, particularly when combined with oral or intramuscular metoclopramide (10 mg). Further, those authors noted a correlation between better pain relief and higher aspirin and salicylate plasma levels. Subsequently, Noda et al, *J. Neurol. Neurosurg. Psychiatry*, 48 (11), 1187 (1985) reported successful treatment of migraine attacks with 497 mg of intravenous aspirin (DL-lysine-acetylsalicylate).

It is believed that aspirin can be successful in treating migraine for two reasons. When taken early in an attack, aspirin may work by inhibiting platelet aggregation, which is thought to be the biochemical trigger of migraine attacks. When administered at a later stage, aspirin or the salicylate it releases may inhibit prostaglandin synthesis and thus help to relieve pain. Nevertheless, there is evidence that early treatment is associated with better relief. See Ross-Lee et al and Noda et al, supra.

In the treatment of severe migraine, fast and reliable relief is of utmost importance. Unfortunately, it appears that aspirin is most effective and works most quickly when given intravenously. This route of administration obviously has its inherent drawbacks, including lack of patient acceptance for esthetic reasons and lack of convenience. For example, intravenous aspirin is typically administered by trained personnel in a hospital setting; it is not suitable for patient self-medication. Moreover, since aspirin is most efficacious when it is administered early in the migraine attack, immediate availability of treatment and ease of administration are especially important.

Oral ingestion would be an ideal route of administration, but absorption from oral dosage forms is slower and more erratic; moreover, vomiting often accompanies migraine, causing loss of part or all of the drug administered. Indeed, since oral aspirin is often irritating to the stomach, oral administration may even increase the tendency toward vomiting.

Rectal dosage forms of aspirin exist and might be useful in treating migraine, but would be impractical when diarrhea accompanies migraine attack. Moreover, rectal dosage forms suffer from lack of patient acceptance for esthetic reasons.

It has recently been proposed that early administration of aspirin to heart attack victims would be very beneficial in limiting damage to the cardiac muscle, due to aspirin's prevention of platelet aggregation in the arteries. During the time immediately following a heart attack, when treatment is most critical, the patient may be unconscious, making oral administration impossible. And, as in the case of migraine, oral absorption can be slow and erratic. On the other hand, intravenous administration may not be practical when it must be undertaken by paramedics in a moving ambulance. And continuation of intravenous therapy during the weeks following a heart attack is impractical, since self-medication by this route would not be feasible.

Thus, while aspirin remains the cornerstone of analgesic therapy for many types of pain, its use in the treatment of relatively severe pain, such as migraine headache and postoperative pain, and its use in the early treatment of heart attack are fraught with difficulties. Migraine and post-operative pain may respond to oral aspirin, but the response is variable and unpredictable. Intravenous administration of neutralized aspirin, on the other hand, has been found to be both effective and reliable in treating post-operative pain and in aborting migraine attacks, but this route of administration requires a skilled operator and is not suitable for patient self-medication.

Previous studies by the present inventor and coworkers have shown that selected drugs, e.g, propranolol, progesterone and estradiol, can be successfully administered nasally. See, for example, Hussain et al, *J. Pharm. Sci.*, 68, 1196 (1979); Hussain et al, *J. Pharm. Sci.*, 69, 1411 (1980); Hussain et al, *J. Pharm. Sci.*, 70, 466 (1981); Hussain et al U.S. Pat. Nos. 4,284,648 and 4,315,925. Numerous other medications have thus far been administered nasally, with varying degrees of success. For an overview of the literature in this area, see "Historical Development of Transnasal Systemic Medications", Y. W. Chien and S. F. Chang, in *Transnasal Systemic Medications*, ed. Y. W. Chien, Elsevier Science Publishers B.V., Amsterdam, 1985, 1–99. However, the previously investigated drugs are structurally remote from aspirin, which has not been previously suggested for nasal administration.

SUMMARY OF THE INVENTION

In view of the foregoing, it is apparent that a need exists for the improved delivery of aspirin, particularly to treat migraine and other types of severe pain and to mitigate the cardiovascular damage resulting from heart attack. Thus, it is an object of the present invention to provide novel dosage forms and a novel method of administering aspirin designed to provide enhanced bioavailability and minimized variations in blood levels as compared to oral aspirin, while at the same time providing relative ease of administration when compared to intravenous injection.

It is a further object of the present invention to provide a novel method and novel dosage forms containing aspirin useful in the treatment of migraine and other types of severe pain and in the mitigation of cardiovascular damage caused by heart attack.

Another object of the present invention is to provide a novel method of administering aspirin which rapidly produces the high blood concentrations of intact aspirin that are required to inhibit platelet aggregation and prostaglandin synthesis.

Yet another object of the present invention is to provide a convenient, non-invasive method for the administration of aspirin which avoids first-pass metabolism, is safe and inexpensive, does not require a skilled operator and yet rapidly produces high blood concentrations of intact aspirin.

The foregoing objects are achieved by nasal administration of neutralized aspirin. According to the invention, the neutralized aspirin is conveniently administered via a novel nasal dosage form, i.e., an aqueous solution, suspension, ointment or gel adapted for nasal administration.

BRIEF DESCRIPTION OF THE DRAWING

The FIGURE of the drawing is a semi-logarithmic plot of mean plasma levels of salicylate in rats following intravenous(■) and intranasal (●) administration of 2 mg doses o aspirin dissolved 0.1 mL of pH 7.4 phosphate buffer.

DETAILED DESCRIPTION OF THE INVENTION

The term "aspirin" as used herein refers to 2-(acetyloxy)benzoic acid, also known as salicylic acid acetate or acetylsalicylic acid, which has the structural formula

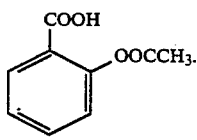

Oral aspirin formulations typically contain from about 300 to about 500 mg per dosage unit. Intravenous aspirin has been formulated containing approximately 500 mg aspirin per vial, the aspirin being used in the form of the amino acid salt, DL-lysine-acetylsalicylate.

The term "neutralized aspirin" as used herein means acetylsalicylic acid in a water-solubilized salt form formulated in neutral aqueous media. Such salt forms include water-soluble stable salts such as the amine salts, for example salts formed by aspirin with amines such as triethanolamine or triethylamine, as well as amino acid salts such as DL-lysine-acetylsalicylate, formulated in aqueous media at neutral pH (pH 7 to 8, approximately). The salts may be prepared by well-known methods and then dissolved in aqueous media appropriate for nasal administration and adjusted, if necessary, to neutral pH, the aqueous media being discussed in more detail hereinbelow. However, it is not necessary to isolate the salt before preparing the nasal composition. In a presently preferred embodiment of the invention, an aqueous solution of the selected base is prepared and the selected dosage of aspirin is simply dissolved in an appropriate volume of the aqueous alkaline solution. Thus, for example, a 7% solution of triethanolamine in water is prepared. Then, to prepare a unit dose for nasal administration, 300 mg of aspirin are dissolved in 4 mL of the triethanolamine solution. Neutralized aspirin may be similarly prepared, for example, from diethylamine, phosphate buffer or acetate buffer, the solution being adjusted as necessary to about neutral to slightly alkaline pH (7 to 8).

In accord with the present invention, it has now been found that aspirin can be very efficiently delivered to the systemic circulation via nasal administration. The following study was undertaken to examine the bioavailability of aspirin from nasal solution as compared to intravenous administration.

Plasma levels of salicylates were studied in rats following intravenous and intranasal administration of 2 mg doses of aspirin dissolved in 0.1 mL of pH 7.4 phosphate buffer.

Male Sprague-Dawley rats, each weighing about 300 g, were used without fasting. For nasal administration, the surgical operation was carried out on the rats as described before [Hussain et al, *J. Pharm. Sci.,* 69. 1411 (1980)] after anesthetizing with pentobarbital sodium (50 mg/kg). The end of the tube which leads from the esophagus to the nasal cavity was closed. The neutralized aspirin solution was administered to the nasal cavity through the nostrils by means of a micropipet and the nostrils were closed with adhesive agent. For intravenous administration, the rats were anesthetized and the neutralized aspirin solution was injected through the femoral vein.

After the administration of the drug, 0.4 mL of blood was sampled periodically from the femoral aorta. The concentrations of salicylates in the blood specimens were determined using a specific HPLC assay. The results, depicted in the FIGURE, demonstrate that aspirin was rapidly absorbed by rats following intranasal administration in accord with the present invention.

Aspirin can be conveniently administered nasally by formulating it into a nasal dosage form comprising the selected form of neutralized aspirin and a nontoxic pharmaceutically acceptable nasal carrier therefor.

Suitable nontoxic pharmaceutically acceptable nasal carriers for use in the compositions of the present invention will be apparent to those skilled in the art of nasal pharmaceutical formulations. For those not skilled in the art, reference is made to the text entitled "REMINGTON'S PHARMACEUTICAL SCIENCES", 17th edition, 1985, as well as to the many recent publications on nasal drug delivery, including Hussain et al U.S. Pat. Nos. 4,284,648 and 4,315,925, and Hussain U.S. Pat. Nos. 4,428,883 and 4,464,378. Obviously, the choice of suitable carriers will depend on the exact nature of the particular nasal dosage form desired, e.g., whether the active ingredient is to be formulated into a nasal solution (for use as drops or as a spray), a nasal suspension, a nasal ointment or cream or a nasal gel. Preferred nasal dosage forms are solutions, suspensions and gels, which contain a major amount of water (preferably purified water) in addition to the active ingredient. Minor amounts of other ingredients such as pH adjusters (e.g., a base such as NaOH), emulsifiers or dispersing agents (e.g., polyoxyethylene 20 sorbitan monooleate), buffering agents, preservatives, wetting agents and jelling agents (e.g., methylcellulose) may also be present. Sustained release compositions, such as sustained release ointments and gels, are of particular interest.

The method and compositions of the present invention may be used in the treatment of any condition for which aspirin can be used, but are especially of interest for the treatment for migraine and for the mitigation of cardiovascular damage resulting from heart attack.

Examples of the preparation of typical nasal compositions are set forth below. However, it is to be understood that these examples are given by way of illustration only and are not to be construed as limiting the invention either in spirit or in scope as many modifications both in materials and in methods will be apparent to those skilled in the art.

EXAMPLE 1

7.5 Grams of aspirin are combined with 90 mL of a 7% solution of triethanolamine in water. The pH is adjusted to about pH 8, the solution is made isotonic with sodium chloride solution and the total volume is brought to 100 mL. The composition contains 300 mg of aspirin per 4 mL.

EXAMPLE 2

Isotonic saline (500 mL) is heated to 80° C. and methyl cellulose (2 g) is added, with stirring. The resultant mixture is allowed to stand at room temperature for 2 hours. Then, 75 grams of aspirin in 450 mL of 7% triethanolamine in isotonic saline is added and the pH is adjusted to about pH 8. A further quantity of isotonic saline sufficient to bring the total volume to 1 liter is added to the gel and thoroughly mixed. The gel contains 300 mg of aspirin per 4 mL.

Naturally, the therapeutic dosage range for nasal administration of the compositions of the present invention will vary with the size of the patient and the condition for which the composition is administered. Moreover, the quantity of nasal dosage form needed to deliver the desired dose will depend on the concentration of aspirin in the composition. A typical unit dose for the treatment of migraine or heart attack is 300 mg every 6 hours.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A method of inhibiting platelet aggregation and/or prostaglandin synthesis in a mammal in need of such treatment which comprises nasally administering thereto an effective platelet aggregation-inhibiting and/or prostaglandin synthesis-inhibiting amount of neutralized aspirin.

2. A method according to claim 1 which comprises nasally administering to said mammal a pharmaceutically acceptable nasal dosage form comprising an effective platelet aggregation-inhibiting and/or prostaglandin synthesis-inhibiting amount of neutralized aspirin and a nontoxic pharmaceutically acceptable nasal carrier therefor.

3. A method according to claim 2, wherein said nasal dosage form is a nasal solution, a nasal suspension, a nasal ointment or a nasal gel.

4. A method according to claim 2, wherein said dosage form is a sustained release nasal dosage form.

5. A method according to claim 2, wherein said dosage form is a sustained release nasal gel.

6. A method according to claim 2, wherein said dosage form is isotonic.

7. A method for the treatment of migraine which comprises nasally administering to a patient in need of such treatment an effective anti-migraine amount of neutralized aspirin.

8. A method according to claim 7 which comprises nasally administering to said patient a pharmaceutically acceptable nasal dosage form comprising an effective anti-migraine amount of neutralized aspirin and a nontoxic pharmaceutically acceptable nasal carrier therefor.

9. A method according to claim 8, wherein said nasal dosage form is a nasal solution, a nasal suspension, a nasal ointment or a nasal gel.

10. A method according to claim 8, wherein said dosage form is a sustained release nasal dosage form.

11. A method according to claim 8, wherein said dosage form is a sustained release nasal gel.

12. A method according to claim 8, wherein said dosage form is isotonic.

13. A method for mitigating cardiovascular damage resulting from heart attack which comprises nasally administering to a heart attack victim an effective amount of neutralized aspirin.

14. A method according to claim 13 which comprises administering to said heart attack victim a pharmaceutically acceptable nasal dosage form comprising an effective amount of neutralized aspirin and a nontoxic pharmaceutically acceptable nasal carrier therefor.

15. A method according to claim 14, wherein said nasal dosage form is a nasal solution, a nasal suspension, a nasal ointment or a nasal gel.

16. A method according to claim 14, wherein said dosage form is a sustained release nasal dosage form.

17. A method according to claim 14, wherein said dosage form is a sustained release nasal gel.

18. A method according to claim 14, wherein said dosage form is isotonic.

19. A pharmaceutically acceptable nasal composition, in dosage unit form, for nasal administration to inhibit platelet aggregation and/or prostaglandin synthesis in a mammal, said composition comprising, per nasal dosage unit, a systemically effective platelet aggregation-inhibiting and/or prostaglandin synthesis-inhibiting amount of neutralized aspirin and a nontoxic pharmaceutically acceptable carrier therefor, said composition comprising a nasal ointment or a nasal gel.

20. A pharmaceutically acceptable nasal composition, in dosage unit form, for nasal administration in the treatment of migraine, said composition comprising, per nasal dosage unit, a systemically effective anti-migraine amount of neutralized aspirin and a nontoxic pharmaceutically acceptable carrier therefor, said composition comprising a nasal ointment or a nasal gel.

21. A pharmaceutically acceptable nasal composition, in dosage unit form, for nasal administration in the mitigation of cardiovascular damage resulting from heart attack, said composition comprising, per nasal dosage unit, a systemically effective amount of neutralized aspirin and a nontoxic pharmaceutically acceptable carrier therefor, said composition comprising a nasal ointment or a nasal gel.

22. A composition according to claim 19, said composition being adapted for sustained release to the nasal mucosa.

23. A composition according to claim 20, said composition being adapted for sustained release to the nasal mucosa.

24. A composition according to claim 21, said composition being adapted for sustained release to the nasal mucosa.

* * * * *